(12) United States Patent
Shaker

(10) Patent No.: US 10,660,653 B2
(45) Date of Patent: *May 26, 2020

(54) DETECTION AND TREATMENT OF ABNORMAL UPPER ESOPHAGEAL SPHINCTER FUNCTIONALITY

(71) Applicant: THE MEDICAL COLLEGE OF WISCONSIN, INC., Milwaukee, WI (US)

(72) Inventor: Reza Shaker, Brookfield, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 7 days.

This patent is subject to a terminal disclaimer.

(21) Appl. No.: 15/349,635

(22) Filed: Nov. 11, 2016

(65) Prior Publication Data

US 2017/0056021 A1 Mar. 2, 2017

Related U.S. Application Data

(62) Division of application No. 13/702,258, filed as application No. PCT/US2011/035050 on May 3, 2011, now Pat. No. 9,526,449.

(Continued)

(51) Int. Cl.
*A61B 17/132* (2006.01)
*A61B 5/00* (2006.01)
(Continued)

(52) U.S. Cl.
CPC ........ *A61B 17/1325* (2013.01); *A61B 5/0002* (2013.01); *A61B 5/037* (2013.01);
(Continued)

(58) Field of Classification Search
CPC ............ A61B 17/1325; A61B 17/1327; A61B 5/4211; A61B 5/0002; A61B 5/24211;
(Continued)

(56) References Cited

U.S. PATENT DOCUMENTS 4,182,344 A 1/1980 Benson
4,230,101 A 10/1980 Gold
(Continued)

FOREIGN PATENT DOCUMENTS

CN 102379733 A 3/2012
WO 03099143 A1 12/2003

OTHER PUBLICATIONS

Almond, et al., A 5-Year Prospective Review of Posterior Partial Fundoplication in the Management of Gastroesophageal Reflux Disease, Int. J. Surg., 2010, 8(3):239-242.
(Continued)

*Primary Examiner* — Patrick Fernandes
(74) *Attorney, Agent, or Firm* — Quarles & Brady LLP

(57) ABSTRACT

An esophageal device is used to recognize, diagnose, characterize, or relieve an impact of an abnormal or defective UES anatomy, physiology, or functionality. In one implementation, the esophageal device measures a UES response to esophageal fluid infusion to detect or characterize an abnormality or defective UES anatomy, physiology, or functionality. An Upper Esophageal Sphincter compression device is used to increase intra-luminal pressure within the Upper Esophageal Sphincter of a patient in order relieve an impact of an abnormal or defective UES anatomy, physiology, or functionality.

14 Claims, 9 Drawing Sheets

Related U.S. Application Data

(60) Provisional application No. 61/352,212, filed on Jun. 7, 2010, provisional application No. 61/418,752, filed on Dec. 1, 2010.

(51) Int. Cl.
| | | |
|---|---|---|
| *A61B 5/103* | (2006.01) | |
| *A61F 2/50* | (2006.01) | |
| *A61B 5/03* | (2006.01) | |
| *A61B 5/07* | (2006.01) | |
| *A61B 17/135* | (2006.01) | |
| *A61B 17/00* | (2006.01) | |

(52) U.S. Cl.
CPC .............. *A61B 5/076* (2013.01); *A61B 5/103* (2013.01); *A61B 5/4211* (2013.01); *A61B 5/4233* (2013.01); *A61B 5/687* (2013.01); *A61B 5/7246* (2013.01); *A61B 17/1355* (2013.01); *A61F 2/50* (2013.01); *A61B 5/0053* (2013.01); *A61B 2017/00022* (2013.01); *A61B 2017/00827* (2013.01)

(58) Field of Classification Search
CPC ..... A61B 5/4233; A61B 5/7246; A61B 5/103; A61B 5/0053; A61B 5/4205; A61F 2/50
See application file for complete search history.

(56) References Cited

U.S. PATENT DOCUMENTS

| | | | |
|---|---|---|---|
| 4,243,028 A | | 1/1981 | Puyana |
| 4,354,503 A * | | 10/1982 | Golden .............. A61B 5/02233 600/490 |
| 4,366,815 A | | 1/1983 | Broomes |
| 4,458,690 A | | 7/1984 | O'Connor et al. |
| 4,479,494 A | | 10/1984 | McEwen |
| 4,553,934 A | | 11/1985 | Armstrong et al. |
| 4,605,010 A | | 8/1986 | McEwen |
| 4,770,175 A | | 9/1988 | McEwen |
| 4,886,070 A | | 12/1989 | Demarest |
| 4,924,862 A | | 5/1990 | Levinson |
| 4,996,720 A | | 3/1991 | Fair |
| 5,024,240 A * | | 6/1991 | McConnel .............. A61B 5/03 600/561 |
| 5,054,494 A | | 10/1991 | Lazzaro et al. |
| 5,091,992 A | | 3/1992 | Pusic |
| 5,123,425 A | | 6/1992 | Shannon, Jr. et al. |
| 5,181,522 A * | | 1/1993 | McEwen ................. A61B 5/03 600/561 |
| 5,280,790 A | | 1/1994 | Brooks |
| 5,366,438 A | | 11/1994 | Martin, Sr. |
| 5,403,266 A | | 4/1995 | Bragg et al. |
| 5,483,974 A * | | 1/1996 | Crangle .................. A61B 5/03 600/587 |
| 5,487,383 A | | 1/1996 | Levinson |
| 5,785,670 A | | 7/1998 | Hiebert |
| 5,840,051 A | | 11/1998 | Towsley |
| 5,904,662 A | | 5/1999 | Myoga |
| 6,056,711 A | | 5/2000 | Domanski et al. |
| 6,200,285 B1 | | 3/2001 | Towliat |
| 6,422,873 B1* | | 7/2002 | Abdelatti .......... A61M 16/0488 434/262 |
| 6,890,285 B2 | | 5/2005 | Rahman et al. |
| 7,052,465 B1 | | 5/2006 | Lunak et al. |
| 7,794,412 B2 | | 9/2010 | Tumbull et al. |
| 8,382,665 B1* | | 2/2013 | Fam ...................... A61B 1/267 128/200.26 |
| 8,640,710 B2 | | 2/2014 | Matthews |
| D724,225 S | | 3/2015 | Maris et al. |
| 9,289,136 B2 | | 3/2016 | Addison et al. |
| 9,468,552 B2 | | 10/2016 | Thibeault |
| 9,526,449 B2 | | 12/2016 | Shaker |
| 2001/0011543 A1 | | 8/2001 | Forsell |
| 2003/0070684 A1* | | 4/2003 | Saied ................ A61M 16/0488 128/869 |
| 2003/0135120 A1* | | 7/2003 | Parks ..................... A61B 5/037 600/463 |
| 2003/0229375 A1* | | 12/2003 | Fleischer ............ A61B 17/1325 606/201 |
| 2004/0097816 A1 | | 5/2004 | Just et al. |
| 2004/0138586 A1 | | 7/2004 | Ganz et al. |
| 2005/0059909 A1 | | 3/2005 | Burgess |
| 2005/0085753 A1* | | 4/2005 | Ducharme ............. A01K 13/00 602/17 |
| 2005/0228302 A1* | | 10/2005 | Dalgaard ........... A61B 5/02208 600/499 |
| 2006/0004304 A1* | | 1/2006 | Parks ..................... A61B 5/037 600/593 |
| 2006/0074362 A1 | | 4/2006 | Rousso et al. |
| 2006/0194179 A1 | | 8/2006 | Abdelatti |
| 2006/0258960 A1* | | 11/2006 | Turnbull ................ A61B 90/06 600/587 |
| 2007/0038132 A1 | | 2/2007 | Kishimoto et al. |
| 2007/0106166 A1* | | 5/2007 | Somberg ........... A61B 5/02233 600/499 |
| 2007/0219588 A1* | | 9/2007 | Freeman .............. A61H 31/005 607/5 |
| 2007/0239092 A1 | | 10/2007 | Ross |
| 2008/0086179 A1 | | 4/2008 | Sharma |
| 2008/0161730 A1* | | 7/2008 | McMahon ........... A61B 5/1076 600/593 |
| 2008/0167675 A1* | | 7/2008 | Hogosta ................ A61B 5/037 606/196 |
| 2008/0262479 A1 | | 10/2008 | Barela |
| 2009/0003669 A1* | | 1/2009 | Parks ..................... A61B 5/037 382/128 |
| 2009/0044799 A1* | | 2/2009 | Qiu ...................... A61B 5/0084 128/200.26 |
| 2009/0187124 A1* | | 7/2009 | Ludlow ................ A61H 39/00 601/47 |
| 2009/0300831 A1 | | 12/2009 | Welch |
| 2010/0022987 A1* | | 1/2010 | Bochenko ........... A61M 5/1454 604/500 |
| 2011/0112448 A1 | | 5/2011 | Wu |
| 2011/0202089 A1 | | 8/2011 | Sun |
| 2012/0150215 A1 | | 6/2012 | Donald |
| 2012/0190938 A1* | | 7/2012 | Addington ............. A61B 5/037 600/301 |
| 2012/0203132 A1 | | 8/2012 | Blumensohn et al. |
| 2013/0090573 A1 | | 4/2013 | Shaker |
| 2013/0102930 A1 | | 4/2013 | Connor |
| 2013/0184621 A1 | | 7/2013 | Ma et al. |
| 2013/0304112 A1 | | 11/2013 | Ting et al. |
| 2014/0257156 A1 | | 9/2014 | Capra et al. |
| 2015/0112380 A1 | | 4/2015 | Heller et al. |
| 2015/0119773 A1 | | 4/2015 | Flannery et al. |
| 2015/0335284 A1 | | 11/2015 | Nuovo et al. |
| 2016/0095605 A1 | | 4/2016 | Maris |
| 2016/0375265 A1 | | 12/2016 | Kim et al. |
| 2017/0258662 A1 | | 9/2017 | Armbrust et al. |

OTHER PUBLICATIONS

Aslam, et al., Performance and Optimal Technique for Pharyngeal Impedance Recording: A Simulated Pharyngeal Reflux Study, American Journal of Gastroenterology, 2007, 102:33-39.

Chang, et al., Systematic Review and Meta-Analysis of Randomised Controlled Trials of Gastro-Oesophageal Reflux Interventions for Chronic Cough Associated with Gastro-Oesophageal Reflux, BMJ, doi:10.1136/bmj.38677.559005.55, Published Dec. 5, 2005, 7 pages.

Chen, et al., Sleep Symptoms and Gastroesophageal Reflux, J. Clin. Gastroenterol., 2008, 42:13-17.

DeLegge, Aspiration Pneumonia: Incidence, Mortality, and At-Risk Populations, Journal of Parenteral and Enteral Nutrition, 2002, 26(6):S19-S25.

Dickman, et al., Relationships Between Sleep Quality and pH Monitoring Findings in Persons with Gastroesophageal Reflux Disease, Journal of Clinical Sleep Medicine, 2007, 3(5):505-513.

(56) References Cited

OTHER PUBLICATIONS

Dimarino, Jr., et al., The Effect of Gastro-Oesophageal Reflux and Omeprazole on Key Sleep Parameters, Alimentary Pharmacology & Therapeutics, 2005, 22:325-329.
Eisenstadt, Dysphagia and Aspiration Pneumonia in Older Adults, Journal of the American Academy of Nurse Practitioners, 2010, 22:17-22.
Ewart, The Efficacy of Cricoid Pressure in Preventing Gastro-Oesophageal Reflux in Rapid Sequence Induction of Anaesthesia, J. Perioper. Pract., 2007, 17(9):432-436.
Farup, et al., The Impact of Nocturnal Symptoms Associated with Gastroesophageal Reflux Disease on Health-Related Quality of Life, Arch. Intern. Med., 2001, 161:45-52.
Fass, et al., Predictors of Heartburn During Sleep in a Large Prospective Cohort Study, Chest, 2005, 127:1658-1666.
Freid, The Rapid Sequence Induction Revisited: Obesity and Sleep Apnea Syndrome, Anesthesiology Clinics of North America, 2005, 23:551-564.
Furnee, et al., Symptomatic and Objective Results of Laparoscopic Nissen Fundoplication After Failed EndoCinch Gastroplication for Gastro-Oesophageal Reflux Disease, European Journal of Gastroenterology & Hepatology, 2010, 22(9)1118-1122.
Gatta, et al., Meta-Analysis: The Efficacy of Proton Pump Inhibitors for Laryngeal Symptoms Attributed to Gastro-Oesophageal Reflux Disease, Alimentary Pharmacology & Therapeutics, 2007, 25:385-392.
Gerson, et al., A Systematic Review of the Definitions, Prevalence, and Response to Treatment of Nocturnal Gastroesophageal Reflux Disease, Clinical Gastroenterology and Hepatology, 2009, 7:372-378.
Hancox, et al., Associations Between Respiratory Symptoms, Lung Function and Gastro-Oesophageal Reflux Symptoms in a Population-Based Birth Cohort, Respiratory Research, 2006, 7:142, 9 pages.
Hunter, et al., A Physiologic Approach to Laparoscopic Fundoplication for Gastroesophageal Reflux Disease, Annals of Surgery, 1996, 223(6):673-687.
King, et al., Trachael Tube Cuffs and Tracheal Dilatation, Chest, 1975, 67:458-462.
Kubota, et al., Tracheal Compression to Prevent Aspiration and Gastric Distension, Can J Anaesth, 1992, 39:2, p. 202.
Kumar, et al., Persistent Pneumonia: Underlying Cause and Outcome, Indian Journal of Pediatrics, 2009, 76 (12):1223-1226.
Landsman, Cricoid Pressure: Indications and Complications, Pediatric Anaesthesia, 2004, 14(1):43-47.
Lawes, et al., The Cricoid Yoke—A Device for Providing Consistent and Reproducible Cricoid Pressure, British Journal of Anaesthesia, 1986, 58(8):925-931.
Locke, et al., Prevalence and Clinical Spectrum of Gastroesophageal Reflux: A Population-Based Study in Olmsted County, Minnesota, Gastroenterology, 1997, 112:1448-1456.
McGuigan, et al., Review Article: Diagnosis and Management of Night-Time Reflux, Alimentary Pharmacology & Therapeutics, 2004, 20(Suppl. 9):57-72.
Mylotte et al., Pneumonia Versus Aspiration Pneumonitis in Nursing Home Residents: Prospective Application of a Clinical Algorithm, J. Am. Geriatr. Soc., 2005, 53:755-761.

Neilipovitz, et al., No Evidence for Decreased Incidence of Aspiration After Rapid Sequence Induction, Can. J. Anesth., 2007, 54:9, pp. 748-764.
Orr, Review Article: Sleep-Related Gastro-Oesophageal Reflux as a Distinct Clinical Entity, Alimentary Pharmacology & Therapeutics, 2010, 31:47-56.
Palombini, et al., A Pathogenic Triad in Chronic Cough—Asthma, Postnasal Drip Syndrome, and Gastroesophageal Reflux Disease, Chest, 1999, 116:279-284.
Parry, Teaching Anaesthetic Nurses Optimal Force for Effective Cricoid Pressure: A Literature Review, Nursing in Critical Care, 2009, 14(3):139-144.
Pfitzner, et al., Controlled Neck Compression in Neurosurgery, Anaesthesia, 1985, 40(7):624-629.
Priebe, Cricoid Pressure: An Expert's Opinion, Minerva Anestesiologica, 2009, 75(12):710-714.
Rakita, et al., Laparoscopic Nissen Fundoplication Offers High Patient Satisfaction with Relief of Extraesophageal Symptoms of Gastroesophageal Reflux Disease, The American Surgeon, 2006, 72:207-212.
Roka et al., Prevalence of Respiratory Symptoms and Diseases Associated with Gastroesophageal Reflux Disease, Digestion, 2005, 71:92-96.
Sale, Prevention of Air Embolism During Sitting Neurosurgery, Anaesthesia, 1984, 39(8):795-799.
Shaker, et al., Nighttime Heartburn is an Under-Appreciated Clinical Problem That Impacts Sleep and Daytime Function: The Results of a Gallup Survey Conducted on Behalf of the American Gastroenterological Association, The American Journal of Gastroenterology, 2003, 98(7):1487-1493.
Shaker, et al., Intrapharyngeal Distribution of Gastric Acid Refluxate, The Laryngoscope, 2003, 113:1182-1191.
Shaker, Nighttime GERD: Clinical Implications and Therapeutic Challenges, Best Practice & Research Clinical Gastroenterology, 2004, 18(S):31-38.
So, et al., Outcomes of Atypical Symptoms Attributed to Gastroesophageal Reflux Treated by Laparoscopic Fundoplication, Surgery, 1998, 124:28-32.
Stroud, et al., Management of Intractable Aspiration, Oct. 18, 2000, 10 pages.
Suiter, et al., Effects of Cuff Deflation and One-Way Tracheostomy Speaking Valve Placement on Swallow Physiology, Dysphagia, 2003, 18:284-292.
Vanner, et al., Upper Oesophageal Sphincter Pressure and the Effect of Cricoid Pressure, Anaesthesia, 1992, 47:95-100.
Wileman, et al., Medical Versus Surgical Management for Gastro-Oesophageal Reflux Disease (GORD) in Adults (Review), The Cochrane Library, 2010, Issue 4, 39 pages.
Young, et al., Evaluation of a New Design of Tracheal Tube Cuff to Prevent Leakage of Fluid to the Lungs, British Journal of Anaesthesia, 1998, 80:796-799.
PCT International Search Report, PCT/US2011/035050, dated Oct. 25, 2011.
PCT International Preliminary Report on Patentability, PCT/US2011/035050, dated Dec. 4, 2012.
Ulualp, et al., Pharyngo-UES Contractile Reflex in Patients with Posterior Laryngitis, The Laryngoscope, 1998, 108 (9):1354-1357.

* cited by examiner

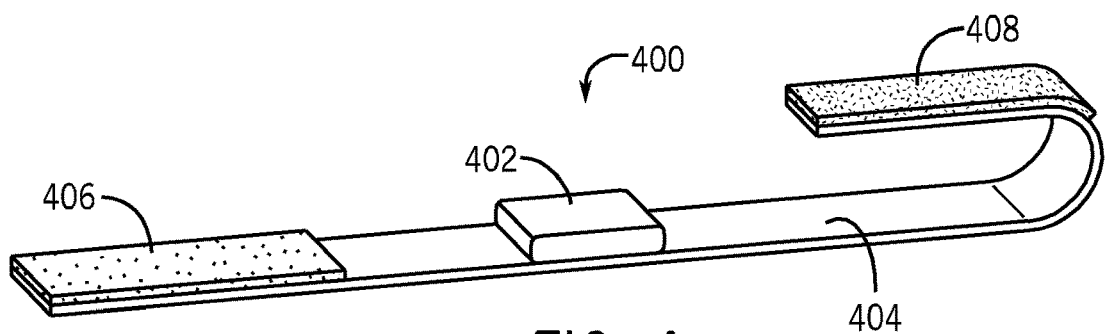
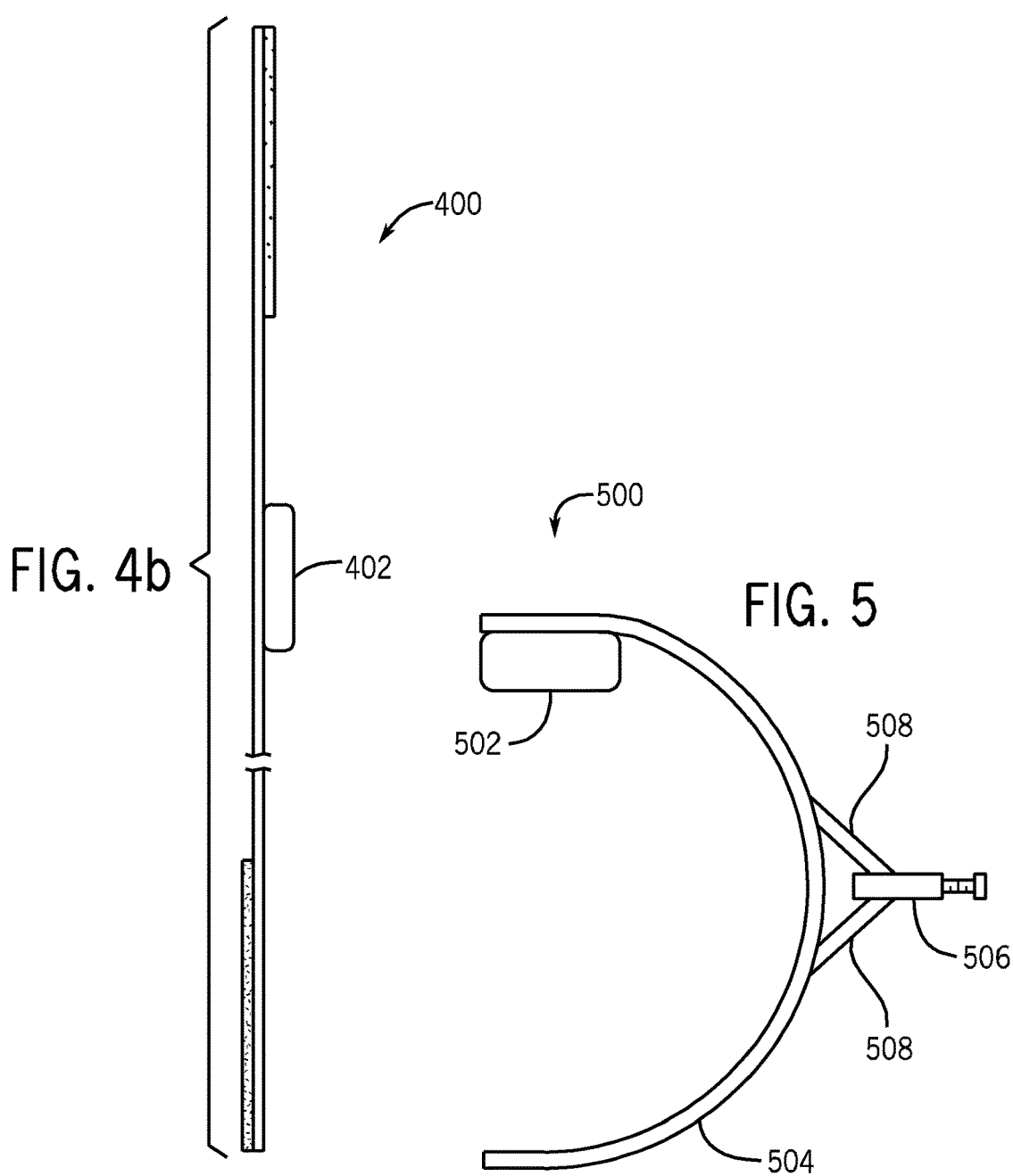

DETECTION AND TREATMENT OF ABNORMAL UPPER ESOPHAGEAL SPHINCTER FUNCTIONALITY

CROSS-REFERENCE TO RELATED APPLICATIONS

This application is a divisional application of U.S. patent application Ser. No. 13/702,258 filed Dec. 5, 2012, which is a 371 application of PCT International Application No. PCT/US2011/035050, filed May 3, 2011, which claims priority to U.S. Application No. 61/352,212, filed Jun. 7, 2010, and U.S. Application No. 61/418,752, filed Dec. 1, 2010.

BACKGROUND

Aspiration of gastric contents into the lung and airway as well as regurgitation of stomach contents into pharynx and larynx (collectively "gastroesophageal reflux") is the reason for a significant number of office visits and hospitalizations. Although morbidity of this condition is not systematically evaluated, a significant percent of deaths has been attributed to the aspiration of gastric content (30-70% of patients with aspiration pneumonia). In addition, a substantial number of outpatient visits are prompted by entry of gastric contents into structures above and beyond the esophagus resulting in various complaints and disorders. These include pneumonia, pneumonitis, bronchitis, laryngitis, pharyngitis, otitis media, laryngeal cancer, dental erosion, and asthma, for example. These conditions cause symptoms such as chronic cough (reflux is the cause in 29% in some studies), frequent throat clearing, sensation of a lump in the throat (globus), excessive phlegm, hoarse voice, ear ache, fever, and productive cough in case of pneumonia.

The most deleterious regurgitation events and aspirations occur in recumbent positions and during sleep. For example, nocturnal acid reflux sufferers often grapple with esophagitis and stricture, adenocarcinnoma of the esophagus, respiratory and Ear Nose and Throat disorders, as well as sleep disturbances and diminished quality of life. These complications during sleep further exacerbate the day-time symptoms of chronic cough, frequent throat clearing, or other symptoms.

To date, despite improvements in acid suppressive therapy, these conditions remain without an effective management and treatment strategy. Studies of effective acid suppression using proton pump inhibitors, H2 receptor antagonists have, at best, reported a modest improvement which has been challenged by properly designed randomized clinical trials. In some instances, pharmacologic therapy has been combined with elevation of the head of the bed or avoidance of eating for three to four hours before retiring to sleep but these methods have not given rise to significant improvements.

Surgical studies of the management of these therapies report success in some patients. These surgical procedures, however, are costly and have some mortality, but significant morbidity including difficulty swallowing, gas bloat syndrome, diarrhea, weight loss, . . . etc. These complications frequently necessitate redo or revision of the operation. In addition, these procedures do not last permanently and lose their efficacy within seven to ten years.

The socio-economic impact of the available medical and surgical therapy for the reflux induced supra esophageal complications and aspirations described above is significant and adds many billions to the health care burden. Accordingly, it would be an advance in the art of health care to provide solutions for gastroesophageal reflux complications.

FIELD

Implementations generally relate to healthcare and more particularly to detection, prevention, and treatment of gastroesophageal reflux complications.

SUMMARY

In certain implementations, an esophageal device for diagnosing Upper Esophageal Sphincter (UES) pathology includes an intra-luminal pressure sensor, a fluid infusion device, and a computing device. The fluid infusion device includes tubing, such as a catheter, and a pump with a controller. The controller controls the pump pressure to inject fluid into the tubing inserted into an esophagus of a patient, invoking a pharyngeal reflux. The computing device receives the intra-luminal pressure when the pharyngeal reflux occurs and compares the intra-luminal pressure with a predetermined intra-luminal pressure. The predetermined intra-luminal pressure is determined from control subjects that experienced a pharyngeal reflux after injection of fluid into their respective esophagi. The computing device outputs results of the comparison for a health care provider (e.g., doctor, physician, surgeon, nurse, or agent thereof) to use in diagnosing the patient. In some implantations, the health care provider prescribes use of a UES compression device. The UES compression device includes a cushion affixed to a band. The band is situated about the neck of the patient to compress against a cricoid of the patient and increase the UES pressure without occluding vital vasculature lateral to the cricoid.

In one implementation, an Upper Esophageal Sphincter (UES) compression kit includes an intra-luminal pressure sensor and a non-invasive device that applies pressure to the UES by external compression to induce a predetermined intra-luminal pressure increase within the UES of a patient. The intra-luminal pressure sensor is located within the esophagus of the patient. When the non-invasive device compresses the UES between the cricoid and the vertebrae, the intra-luminal pressure sensor detects the change in intra-luminal pressure.

In another implementation, the compression device includes a cushion and a band that is coupled to the cushion. When the band is in tension around the neck of a sleeping patient, the cushion is compressed towards the cricoid of the sleeping patient inducing an intra-luminal pressure increase within the UES to a predetermined pressure amount. The compression device may also include means to vary the tension of the band.

BRIEF DESCRIPTION OF THE DRAWINGS

Implementations will become more apparent from the detailed description set forth below when taken in conjunction with the drawings, in which like elements bear like reference numerals.

FIG. 4a is a schematic diagram showing a perspective view of yet another exemplary implementation of the device that compresses the UES of the patient;

FIG. 4b is a schematic diagram showing a side view of the device of FIG. 4a;

FIG. 5 is a schematic diagram depicting another exemplary implementation of the device that compresses the UES of the patient;

FIG. 6b is a schematic diagram showing a perspective elevational view of an exemplary UES compression device of FIG. 6a;

FIG. 7b is a schematic diagram showing a side view of the cushion of FIG. 7a;

DETAILED DESCRIPTION

A non-pharmacologic device is used to increase intra-luminal pressure within the Upper Esophageal Sphincter (UES) of a patient, such as a human or animal, in order to prevent entry of gastric contents into the pharynx, larynx, or a lung. The device uses external pressure to induce intra-luminal pressure within the UES, by compressing the UES between a cricoid cartilage and a cervical vertebrae and preventing gastroesophageal reflux. The induced intra-luminal pressure, however, does not occlude the esophagus under all physiological events. Such occlusion can result in morbidity or mortality. For example, excess external pressure may damage the underlying tissue or compromise the ability of the UES to open to vent gas or belch, or to allow swallowing or high pressure vomiting. Here, the device is used to maintain the intra-luminal pressure of the patient within a predetermined range, continuously reinstating the competency of the UES over a period of time. In certain implementations, the intra-luminal UES pressure is induced by applying an external pressure to a patient's cricoid transferring a compressive force through the intermediary tissue of the patient towards the UES, increasing its intra-luminal pressure. The terms "UES compression device," "compression device," or "device" or UES assist device are used interchangeably herein.

In certain implementations, the intra-luminal UES pressure is kept within the predetermined range while the patient is asleep. Normal resting pressure of the UES is about 40 mm Hg in the elderly and about 70 mm Hg in the young. The driving pressure of the majority of reflux events are less than 20 mm Hg. During sleep, the intra-luminal UES pressure may decline to approximately 10 mm Hg, potentially rendering the UES incompetent to maintain the barrier against aspiration. Here, the device may be used to induce the intra-luminal pressure to remain within a range that is about 10-70 mm Hg, such as about 20-40 mm Hg during sleep, for example. Therefore, the induced intra-luminal pressure effectively prevents gastroesophageal reflux from entering the pharynx and subsequently in the larynx and the lung during sleep. The terms "UES pressure," "intra-luminal pressure," and "intra-luminal UES pressure" are used interchangeably herein.

Figure 1:
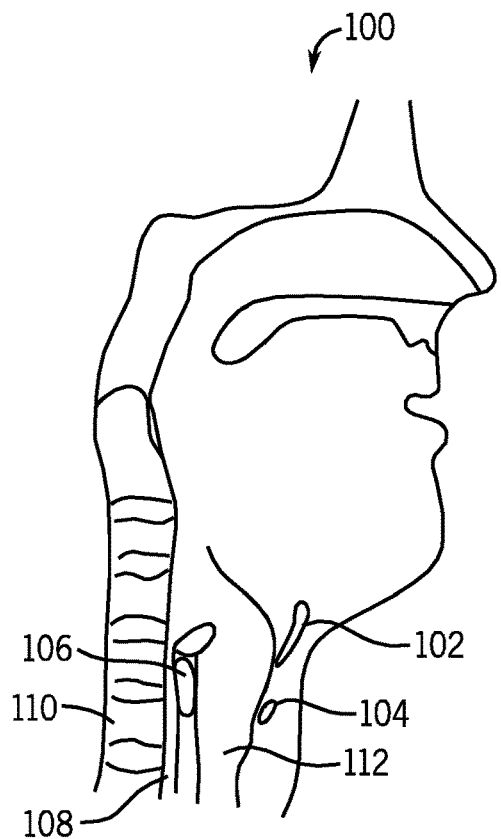
FIG. 1 is a schematic diagram depicting a sagittal cross section of a nose, mouth, pharynx, and larynx of a patient.

Referring to FIG. 1, a schematic diagram depicting a sagittal cross section 100 of a nose, mouth, pharynx, larynx, and esophagus of a patient. The cricoid cartilage is a semi-circular cartilage just above the trachea 112. The posterior portion of the cricoid 106 is located just anterior to the UES of the esophagus 108 and is typically broader than the anterior portion of the cricoid 104 that sits just inferior to the thyroid cartilage 102 (Adam's apple) in the neck. The crico-pharyngeous muscle, the main component of the UES (not shown) is a "C" clamp-shaped muscle that attaches to the posterior lamina of the cricoid just distal to the thyroid cartilage 102. Behind the crico-pharyngeous muscle is the cervical vertebrae 110. Therefore, crico-pharyngeous muscle, the main component of the UES and chief barrier against reflux and aspiration into the airway, is located between the vertebrae and the cricoid cartilage giving rise to the opportunity for increasing the UES intra-luminal pressure by external application of pressure onto the cricoid cartilage.

Determining a value for the external pressure that can induce the increase in the intra-luminal pressure to stay within the predetermined range is a challenge because externally applied pressure propagates to the esophagus differently among patients. For example, in some patients, the cricoid becomes calcified or even ossified with age. In others, the soft tissue over the cricoid may have different thickness. The size of the neck may have an effect. Applying an external pressure of 40 mm Hg to the ossified cricoid of an elderly patient, for example, will induce a different intra-luminal pressure than applying the external pressure of 40 mm Hg to a pediatric patient. Therefore, there is no one-on-one correlation between an externally applied pressure and the intra-luminal pressure that is universal across patients.

In one implementation, a non-invasive UES compression device is used in conjunction with an intra-luminal pressure sensor (collectively "UES compression kit") to determine an association (e.g., correlation) between the external pressure and the intra-luminal pressure that is induced to be within the predetermined range for a specific patient. Once the correlation is known, the non-invasive UES compression device can be used to set the intra-luminal pressure of the patient within the predetermined range without reusing the intra-luminal pressure sensor.

Figure 2:
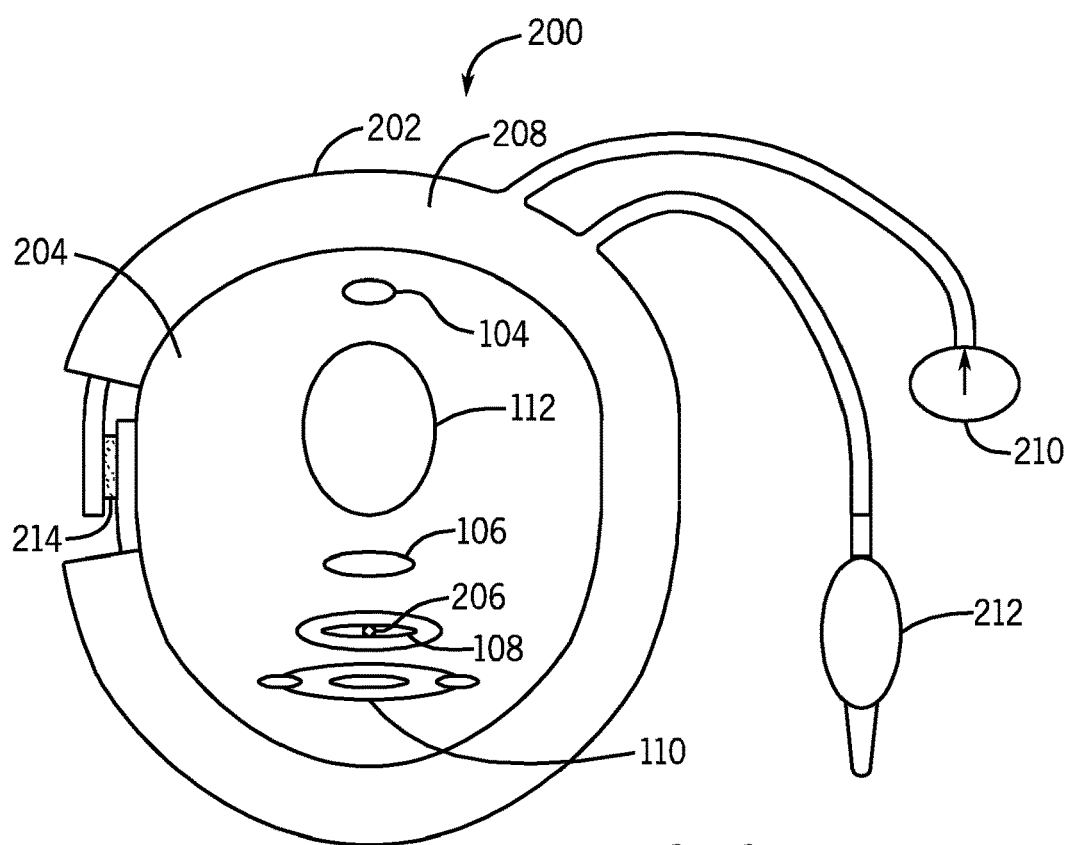
FIG. 2 is a schematic diagram depicting a transverse cross section of a patient's neck encircled by one exemplary implementation of a device that compresses the UES of the patient and further depicting an intra-luminal pressure sensor within the esophagus of the patient.

Referring to FIG. 2, a schematic diagram depicts a transverse cross section 200 of the UES compression kit applied to a patient's neck 204. Here, an exemplary implementation of the UES compression device 202 encircles the patient's neck 204 and an intra-luminal pressure sensor 206 is inserted into the esophagus 108 of the patient. Other implementations are also possible.

The intra-luminal pressure sensor 206 of the UES compression kit may be any form of pressure sensor known to those of ordinary skill in the art. For example, the intra-luminal pressure sensor 206 may be a manometer that is catheterized into the esophagus 108. The intra-luminal pressure sensor 206 may employ any number of means to measure pressure such as piezoelectric sensors or liquid column gauges, for example.

The UES compression device 202 in FIG. 2 is illustrated as having an inflatable cuff 208, a gauge 210, and a bulb 212 for manual insertion of pressurized air into the inflatable cuff 208. The inflatable cuff 208 can be inflated by squeezing the bulb 212. The pressure produced by the cuff 208 can then be read using the gauge 210. The gauge 210 may be connected to the cuff 208 via a tube that is long enough for the patient to be able to read the gauge 210. In other implementations, the bulb 212 may be replaced with means to automatically insert pressurized air into the inflatable cuff 208, such as an air pump.

The internal structure of the inflatable cuff 208 may also vary among different implementations. For example, the internal structure of the inflatable cuff 208 may have one or more balloons (e.g., inflated diameter of about 2 cm) and tubes that distribute the air in a manner that would optimally compress the UES while applying a limited, non-significant amount of pressure on the blood vessels in the neck, such as the carotid artery on the lateral side of the neck. In another implementation, the inflatable cuff 208 periodically, partially deflates at set intervals automatically. This may be employed to achieve higher external pressure of above 30 mm Hg, for example.

The inflatable cuff 208 may have a coupling means 214 to couple the two ends of the inflatable cuff together when wrapped around the neck of the patient. Examples of the coupling means 214 include a hook-and-loop fastener, a fastener with female and corresponding male connectors, or mechanical securement devices, for example.

Figure 3:
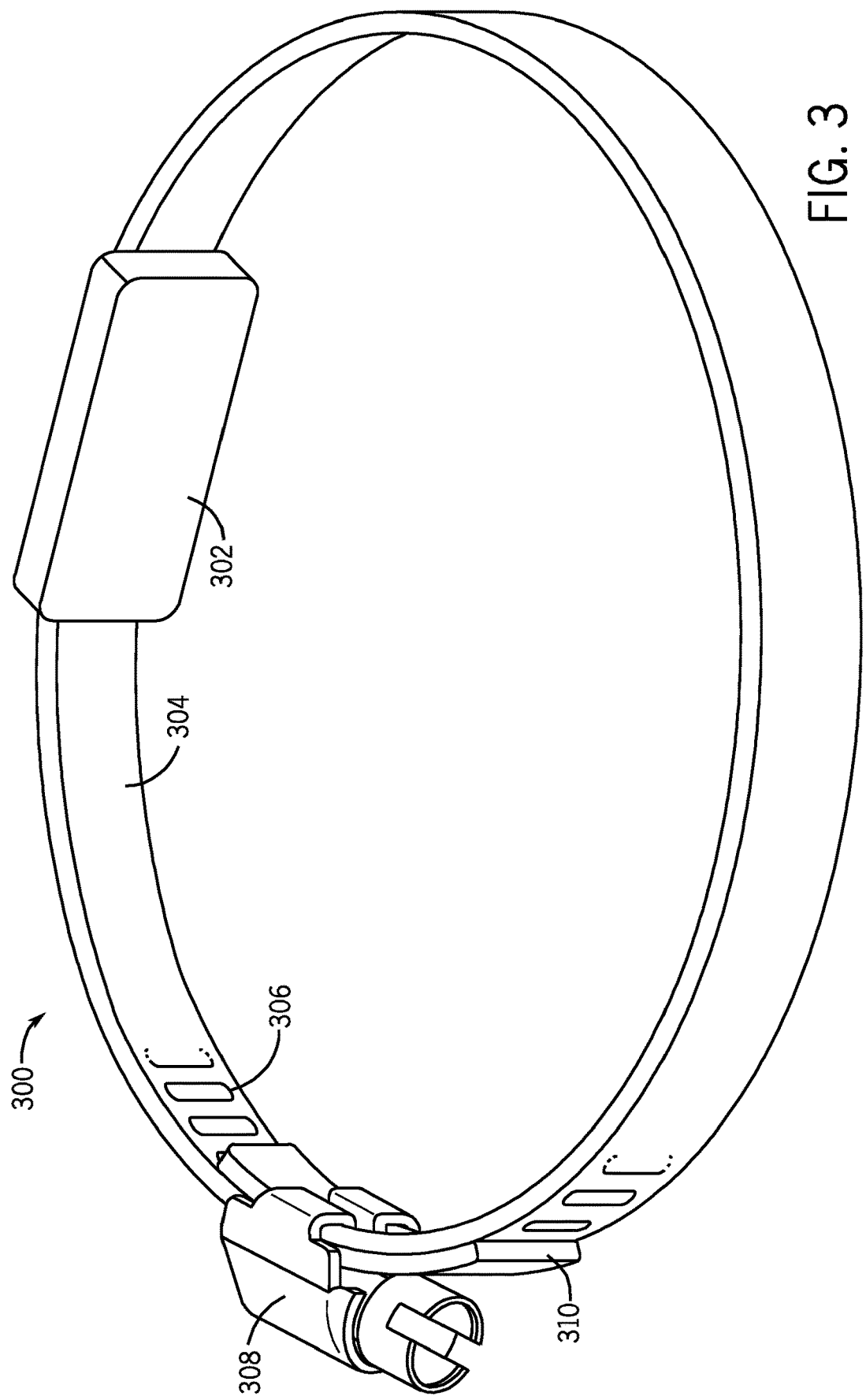
FIG. 3 is a schematic diagram depicting another exemplary implementation of the device that compresses the UES of the patient.

Referring to FIG. 3, another implementation of the UES compression device 300 is depicted. Here, the compression device 300 includes a cushion 302 that is coupled to a band 304. The cushion 302 may be about ½ to 1 inch in width, ½ to 1 inch in thickness, and about 2 inches long. Other configurations and shapes of the cushion are also contemplated. The exterior surface of the cushion 302 can be made of soft, biocompatible material that reduces the potential of irritation sensation or infection when the cushion 302 of the UES compression device 300 is brought into contact with the skin of the patient. For example, the cushion 302 or its exterior may be made of a polyurethane derivative. Similarly, the cushion 302 may act, but need not act, as a buffer that diffuses the compressive forces of the band against the patient's neck. The cushion 302, or other parts of the UES compression device 300, may be disposable such that it is replaced prior to further use.

The band 304 may be made of any durable material. For example, the band 304 may be made of cloth, an elastomer, metal, plastic, or other material or combinations thereof. In certain implementations, the band is between about 0.5-2 inches in width and about 0.5-3 feet in length. In FIG. 3, the band 304 has notches 306 or screw thread patterns that are cut or pressed into the band 304. One or more captive screws 308 are used to tighten the band around a patient's neck. The band 304 is placed around the neck of the patient and the loose end 310 of the band 304 is fed into a space between the band 304 and the captive screw 308. The captive screw 308 is tightened acting as a worm drive that pulls the notches 306 or threads of the band 304, causing the band 304 to tighten around the neck of the patient.

Referring to FIGS. 4a and 4b, another implementation of the UES compression device 400 is depicted. FIG. 4a is a perspective elevational view and FIG. 4b is a side view of the UES compression device 400. Similar to the UES compression device 300, the UES compression device 400 includes a cushion 402 and a band 404. Here, the UES compression device 400 employs a hook-and-loop means (e.g., a Velcro® fastener) to couple the first end 406 and second end 408 of the band 404 together. The first end 406 is shown in FIG. 4a as the loop end and the second end 408 is shown as the hook end of the hook-and-loop fastener.

Once coupled, the length along the long axis of the band 404, of the UES compression device 400 is directly related to the intra-luminal pressure. Alternatively, or in combination, the length is varied to obtain the desired intra-luminal pressure by applying less external pressure.

In certain implementations, the length of the cushion 402 along the long axis of the cushion 402 and a thickness of the cushion 402 is configured to apply minimal external pressure to the vascular structures within the neck, such as the carotid artery or the jugular veins. For example, the thickness of the cushion 402 allows for a gap of air between the compression device 400 and the neck in the proximity of the vascular structures. Here, the band 404 bridges over the carotid and jugular vein avoiding compression of these vital organs. The aforementioned bridge is between the cushion and sternocleidomastoid muscle.

Yet another implementation of the UES compression device 500 is illustrated in FIG. 5. Here, the UES compression device 500 includes a cushion 502 located at one end of a band 504, shown as a cricoid yoke, and a tightener 506. The band 504 is made of stiff material such as metal or hard plastic. The UES compression device 500 can be positioned in a coronal plane or sagittal plane about the neck of the patient such that the cushion 502 is in contact with the anterior surface of the patient's neck over the cricoids. When the tightener 506 is twisted, the wings 508 of the tightener 506 are brought together reducing the angle there between. The reduction of the angle puts a force on the band 504, bringing its two ends together and compressing the cushion 502 against the cricoid of the patient.

Figure 6A:
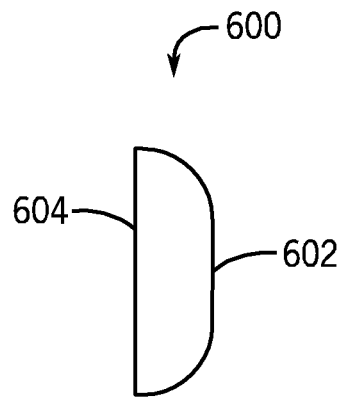
FIG. 6a is a schematic diagram showing a side view of the exemplary UES compression device.
Figure 6B:
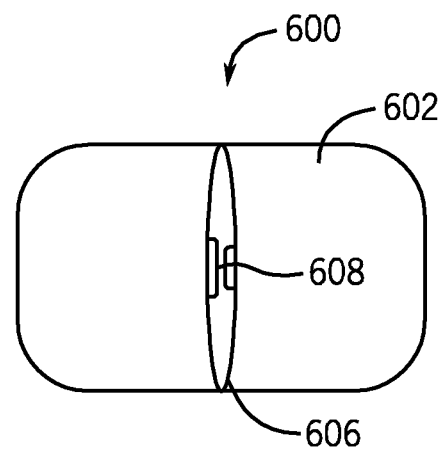

Referring to FIGS. 6a and 6b, another implementation of the UES compression device 600 includes a cushion 600. The cushion 600 has a medial 604 and a lateral 602 side. The medial 604 side has a temporary adhesive that can be put into contact with the anterior portion of the patient's neck, over the cricoid. The cushion 600 has a pouch 606 through which the content of the cushion can be increased or decreased, changing its weight. For example, small bags of sand or other materials can be put into the cushion 600 until the desired weight is achieved. The pouch 606 has a closing means 608, such as a latch or fastener, that closes the pouch when the content is at the desired weight. Here, the UES compression device 600 compresses the patient's cricoid when the patient is in the supine position because the weight of the pouch presses against the cricoid.

The implementations disclosed are non-limiting. Other implementations are also contemplated. For example, the implementation in FIG. 3 may have a different type of coupling means that resembles the clasp of a belt buckle, or the material of the UES compression device 400 may be elastic. Moreover, the features of the various implementations may be mixed and matched such as utilizing the tightening means in one implementation in another implementation.

Figure 7A:
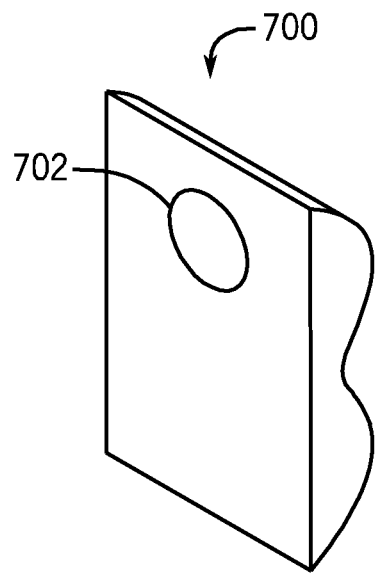
FIG. 7a is a schematic diagram showing a perspective elevational view of an exemplary cushion used to compress the UES of the patient.
Figure 7B:
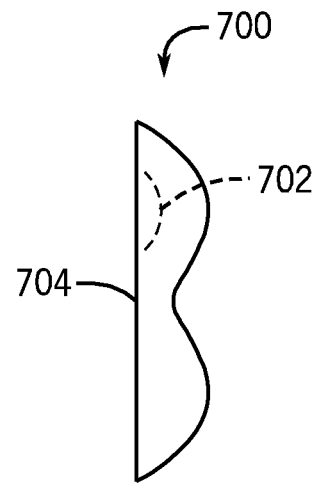

FIGS. 7a and 7b illustrate an implementation of the cushion 700 that might be employed with the UES compression device, such as the UES compression devices 200-600. FIG. 7a is a perspective view and FIG. 7b is a side view of the cushion 700. The cushion 700 has a recession 702 that dimples the medial 704 portion of the cushion 700.

When the cushion 700 is placed over the anterior portion of the patient's neck, the recession 702 is positioned over the tracheal cartilage ("Adam's Apple") of the patient's neck and the area just beneath the recession 702 is positioned over the cricoid. In this manner, recession 702 can act as an anchor, preventing displacement of the cushion during sleep. This can assist in maintaining the pressure against the cricoid within the predetermined range.

Figure 8:
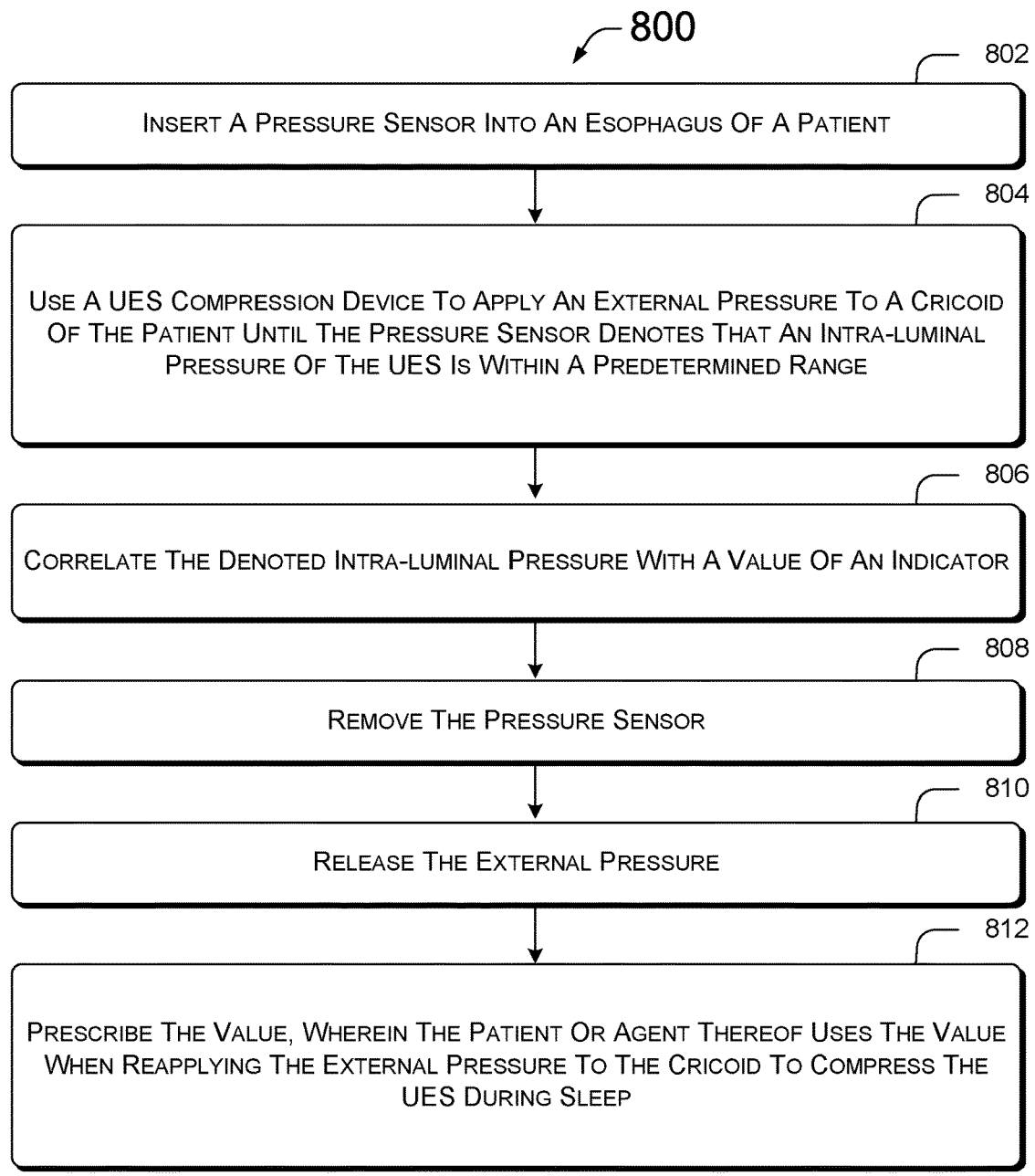
FIG. 8 is summary of a method for compressing the UES of a patient to reduce gastroesophageal reflux.

Referring to FIG. 8, a flow diagram summarizes a method 800 for compressing the UES of a patient to reduce gastroesophageal reflux during sleep. At step 802, an intra-luminal pressure sensor is inserted into the esophagus of a patient. For example, a manometer may be catheterized into the esophagus of the patient through the nose of the patient. A base value of the intra-luminal pressure may be measured in a standing position, in a sitting position, or in a lying down position.

At a step 804, the UES compression device is used to apply an external pressure to the cricoid of the patient. The external pressure is varied until the intra-luminal pressure sensor denotes that the intra-luminal pressure of the UES is within a predetermined range, such as between about 10-70 mm Hg. This predetermined range is ideally in a range that allows the UES to open to vent gas or allows belching, or allows swallowing or high pressure vomiting.

At a step 806, the intra-luminal pressure of the patient is correlated with a value of an indicator that is associated with the applied external pressure. In this manner, the relationship between the external pressure and the intra-luminal pressure for that specific patient is known.

The value of the indicator may depend on the implementation of the UES compression device being employed. For illustrative purposes only, the following provide exemplary potential values that can be correlated to a desired intra-luminal pressure for the implementations disclosed above. In the implementation of the UES compression device depicted in FIG. 2, the value of the external pressure measured by the gauge 210 that induces 20 mm Hg of intra-luminal pressure is identified. In the implementation of FIG. 3, the number of notches 306 on the band 304 that result in 40 mm Hg of intra-luminal pressure is identified. In the implementation of FIG. 4, the relative position of first end 406 coupled to the second end 408 of the band 404 that induces 30 mm Hg of intra-luminal pressure is identified. In the implementation of FIG. 5, the amount that the tightener 506 is twisted to produce 25 mm Hg of intra-luminal pressure is identified. In the implementation of FIG. 6, the weight of the cushion 600 that induces 30 mm Hg of intra-luminal pressure in a supine patient is identified. Other values of indicators are also contemplated.

At the steps 808 and 810, the intra-luminal pressure sensor is removed and external pressure is removed, respectively. At the step 812, the value for the indicator is prescribed. The patient, or agent thereof, can use the value when reapplying the external pressure to the cricoid with the UES compression device to compress the UES for a duration of time, such as during sleep for example. In this manner, the intra-luminal pressure sensor does not need to be reinserted to determine if the appropriate external pressure is being applied to induce the intra-luminal pressure that is within the predetermined range.

To illustrate, a practitioner (e.g., a nurse or doctor) may use the UES compression kit to determine a prescription to reduce gastroesophageal reflux in a patient during sleep. The practitioner catheterizes the intra-luminal pressure sensor (step 802) and uses the UES compression device 400 to induce a desired intra-luminal pressure in a supine patient (step 804). The practitioner marks the band 404 to indicate to what degree the band is to be tightened to reproduce the desired intra-luminal pressure (step 806). For example, the mark can indicate the length of the anterior portion of the first end 406 that is to be coupled to the posterior portion of the second end 408. After removing the intra-luminal pressure sensor (step 808) and the UES compression device 400 (step 810), the practitioner prescribes that the UES compression device 400 is to be intermittently worn at the marked length by the patient for a duration, such as during sleep (step 812). The prescription may be for the patient to use the UES compression device for a period of time, such as several days (nights), weeks, months, years, or a lifetime.

In some implementations, the patient may return to repeat the steps 802 through 812. For example, the material of the band or cushion of the compression device may creep or wear over time or the patient's anatomy may change (e.g., weight, age . . . etc.). Here, the correlation between the value of the indicator and the intra-luminal pressure may be updated or the compression device replaced. Therefore, from time to time, the prescription may need adjusting and/or a new prescription may need to be given.

Figure 9:
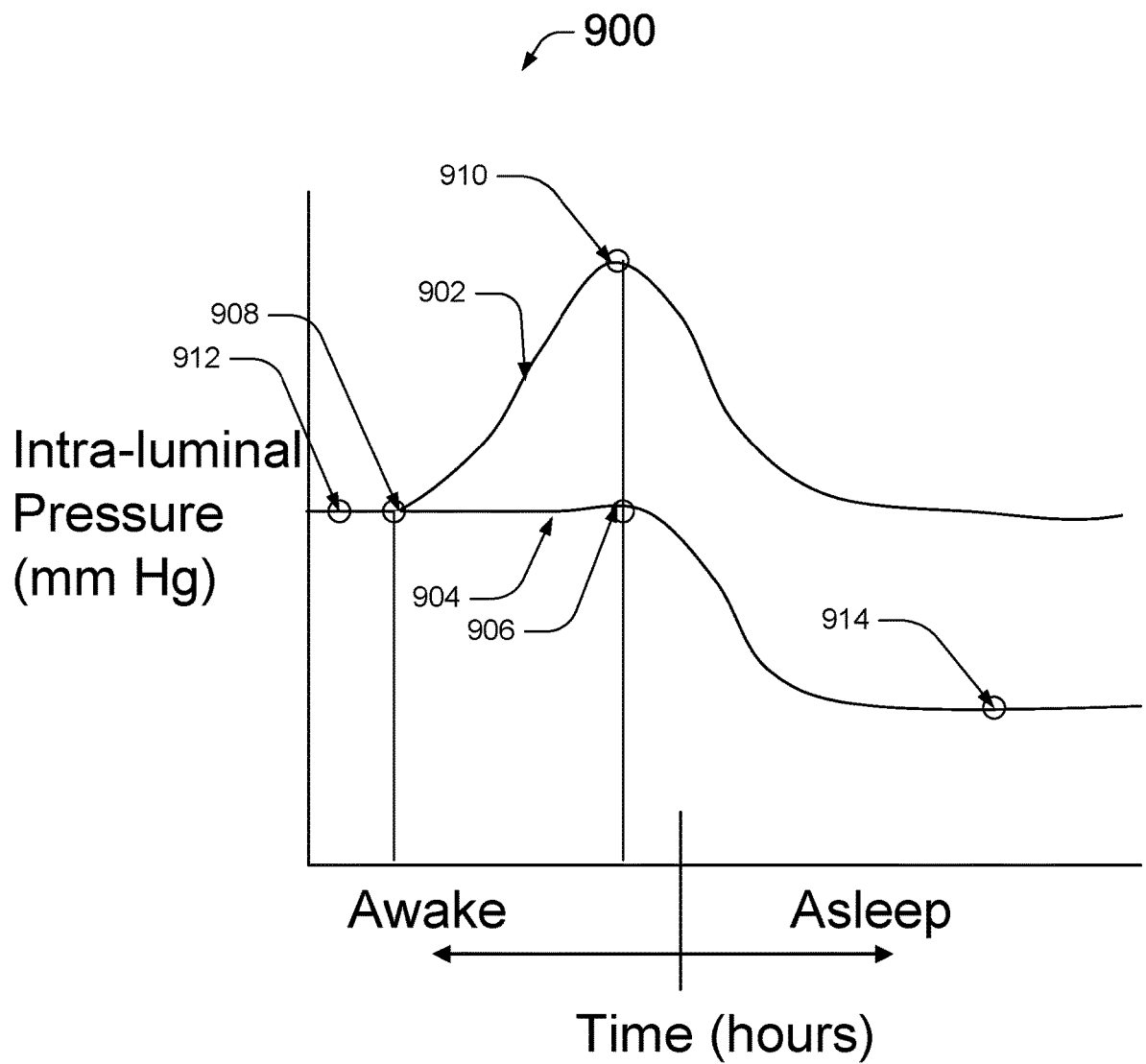
FIG. 9 is a graph depicting variations in intra-luminal pressure during awake and sleep stages of a patient suffering from gastroesophageal reflux.

Referring to FIG. 9, a graph depicts variations in pressure; the UES during awake and sleep stages of a patient suffering from gastroesophageal reflux. The Y-axis depicts the intra-luminal pressure in mm Hg and the X-axis depicts time measured in hours. The two graph lines show the intra-luminal pressure of the patient using a UES compression device (graph line 902) and not using a UES compression device (graph line 904). The resting level of the intra-luminal pressure for the patient is denoted at pressure 912, which is typically about 40 mm Hg. For the patient using the UES compression device, the compression device begins applying pressure to the cricoid of the patient at time 908 shown on graph line 902. The intra-luminal pressure is increased until the value of the indicator is at a prescribed level 910. At time 906, the patient begins to fall asleep. For the patient using the UES compression device, as the patient falls asleep the intra-luminal pressure decreases to the predetermined level that is induced by the compression device. In contrast, for the patient not using the UES compression device, the intra-luminal pressure decreases to approximately 10 mm Hg or below and remains at approximately 10 mm Hg or below (graph line 904 at pressure level 914) throughout the sleeping stage, leaving the patient susceptible to another episode of gastroesophageal reflux. Graph line 902 in FIG. 9 shows the rise in intra-luminal pressure to be about equal to the fall in intra-luminal pressure as the patient using the compression device falls asleep. However, the rise and fall may have different values (e.g., 30 mm Hg rise as the patient tightens the compression device and 20 mm Hg fall as the patient falls asleep or visa versa).

Figure 10:
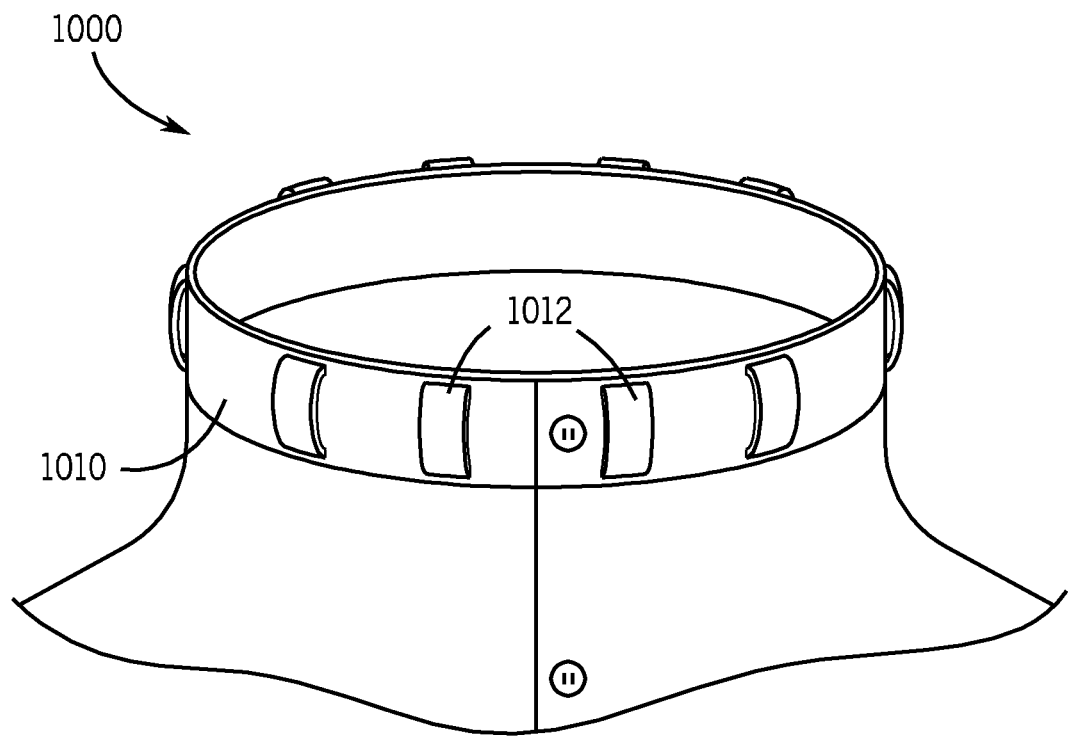
FIG. 10 is a schematic diagram showing a garment for use with a device that compresses the UES of the patient.
Figure 11:
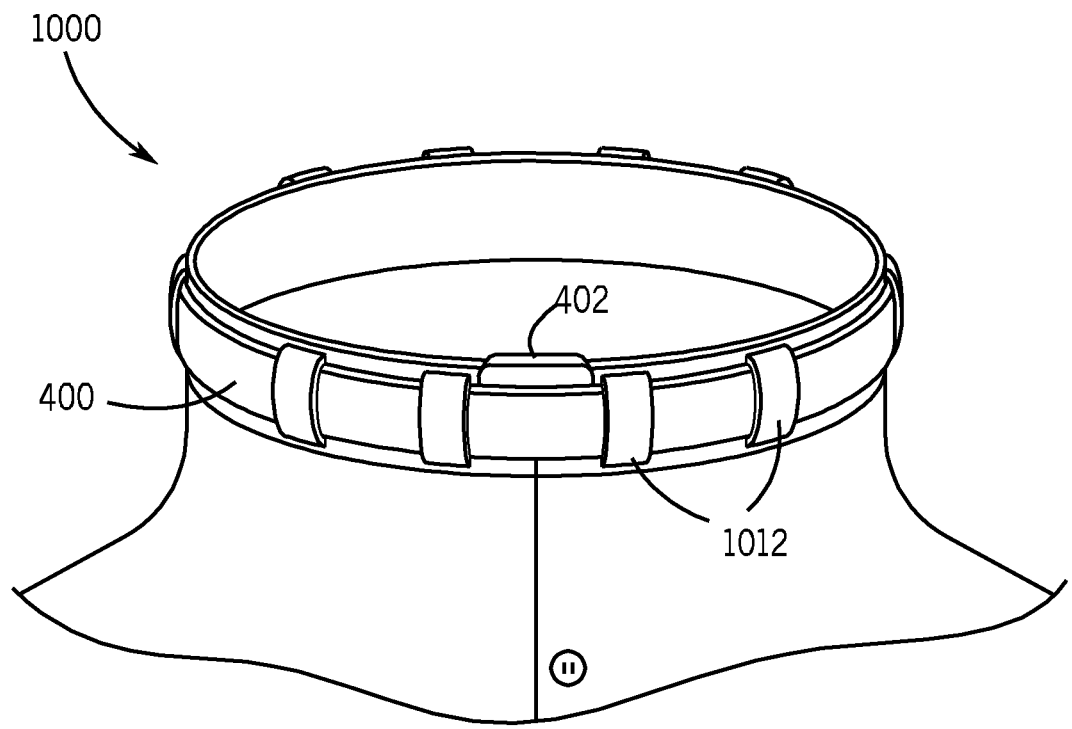
FIG. 11 is a schematic diagram of the garment in FIG. 10 with the device temporarily affixed to the garment.

In certain implementations, the UES compression device is used to increase the intra-luminal pressure while the patient is asleep, raising the intra-luminal pressure from approximately 10 mm Hg to approximately 40 mm Hg, for example. Referring to FIGS. 10 and 11, the compression device 1102 is temporality affixed to a garment 1000, such as a shirt or a sleeping garment, through a plurality of loops 1012 of collar 1010 of the garment 1000. Here, movement of the compression device 400 during sleep, for example, is reduced because the compression device 400 is affixed to the garment, maintaining its a position about the neck of the patient.

In certain implementations, the UES compression device is reusable. In other implementations, the UES compression device is disposable.

Detection of Abnormal UES Functionality

An esophageal device may be used to conduct an esophageal stimulation test to recognize, diagnose, or characterize an abnormal or defective UES anatomy, physiology, or functionality. An esophageal distention, such as through an introduction of liquid or gas into the esophagus via the nose, mouth, or ears, can induce an UES contractile reflex in a subject, such as a healthy or diseased patient. This reflex is likely part of a complex physiological mechanism that protects the airway from retrograde aspiration, for example. The Esophago-UES Contractile Reflex in diseased patients may be dissimilar to those in healthy patients, implying an abnormality in the UES anatomy, physiology, or functionality.

In certain implementations, the esophageal stimulation test includes determining a pressure response of the UES ("UES response") to an esophageal distension in each of an asymptomatic, control subject and a patient with complaints of, for example, regurgitation, reflux-attributed supraesophageal complications ("symptomatic patient"), laryngitis, hoarse voice, or chronic cough. The corresponding pressure responses of the UES for each of the symptomatic patient and the control subject can be compared to one another to evaluate a degree of defectiveness or abnormality of the UES of the symptomatic patient. In some embodiments, the UES response to intraesophageal fluid injection in patients is different from age matched control subjects due, in part to, a periodic spontaneous UES pressure drop below baseline. For example, the UES response (e.g., the UES pressure) of a female, symptomatic patient with a partial esophagectomy and gastric pull-up is compared with the UES response of an asymptomatic, control subject to show the differences in the UES response. Alternatively, or in combination, the UES response of the symptomatic patient can be compared with the UES response of an arithmetic combination (e.g., average) of a plurality of UES responses of a plurality of corresponding control subjects.

Figure 12:
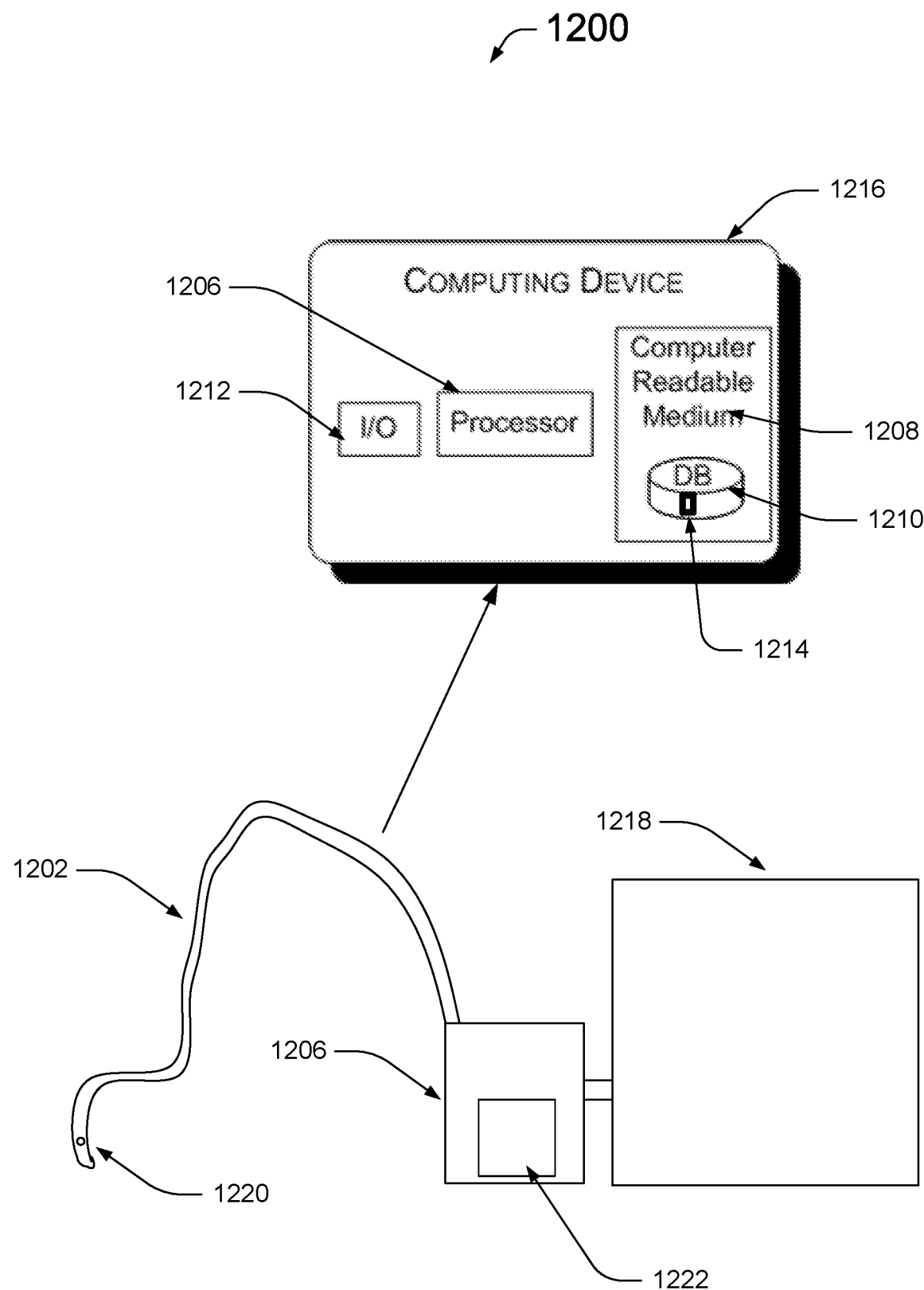
FIG. 12 is a schematic of an esophageal device for diagnosing UES pathology.

FIG. 12 is a schematic diagram that illustrates an esophageal device 1200 that includes a tubing 1202 (e.g., a catheter 1202), a pump 1206, a controller 1222 configured to control a pump pressure of the pump 1206, a fluid source 1218, and computing device 1216. Although a single tubing 1202, pump 1206, controller 1222, fluid source 1218, and computing device 1216 are shown in FIG. 12, it will be apparent that any number of tubing 1202, fluid sources 1218, pumps 1206, controllers 1222, and computing devices 1216 can be part of the esophageal device 1200. In certain implementations the tubing 1202, the pump 1206, the controller 1222, and the computing device 1216 is collectively referred to as "a fluid infusion device."

According to a certain implementation, the intra-luminal pressure sensor 1220 is part of tubing 1202. For example, a UES sleeve catheter (Dentsleeve®, Adelaide®, or Australia® catheter) incorporates a sleeve device (about 6×0.5×0.3 cm) and side hole recording ports at its proximal and distal ends for manometric positioning. The sleeve assembly has additional recording sites at about 4.5, 7, and 14 cm distal and about 3 cm proximal to the sleeve. In other implementations, the intra-luminal pressure sensor 1220 is affixed to a second tube or catheter such that it is separate from the fluid infusion device depicted in FIG. 12.

The fluid source 1218 may be a volume configured to house a fluid, such as normal saline, water, air, a fluid with the same viscosity as normal saline at room temperature, or a combination thereof, for example. Other fluids are also contemplated as would be known by those of ordinary skill in the art. The fluid source 1218, may be an intravenous bag, a box, or other container capable of housing the fluid. Alternatively, or in combination, the fluid source 1218 may be a connection to a plumbing of a building, such as a nozzle to a water source in a doctor's office.

The pump 1206 may be any conventional pump capable of infusing fluid through the tubing 1202. For example, the pump 1206 may be a Harvard® infusion pump (model N0975; Harvard Apparatus Co., Dover, Mass.).

The controller 1222, controls a pump pressure of the pump 1206. To illustrate, the controller 1222 may be a dial that electronically controls an aperture of a valve. In another example, the controller 1222 may include a driver that autonomically controls a pump pressure, a rate of change of the pump pressure, a sequence of predetermined rates of change of the pump pressures, or a combination of the foregoing. For example, the controller 1222 may be programmed to automatically or autonomically implement a sequence of pressures such as: about 0.05 mL/second of fluid injection over a first period of time necessary to infuse 60 ml of normal saline or any other harmless fluid marked with color to make it detectable by endoscopic visualization or detection by impedance monitoring commercially available, followed by a rest interval (e.g., 20 to 30 seconds) of no fluid injection, followed by a pressure that delivers about 0.1 mL/second of fluid injection, followed by a rest interval of no fluid injection, followed by fluid injection of about 1 ml, followed by 2 ml, followed by 3 ml, and 5.5 mL/min of a volume of 60 ml of fluid injection. Rate and amount of infusion may be varied to increase the possibility of detection of pharyngeal reflux.

In some embodiments, the computing device 1216 may be an article of manufacture such as a server, a mainframe computer, a mobile telephone, a personal digital assistant, a personal computer, a laptop, or other special purpose computer, for example, having one or more processors (e.g., a Central Processing Unit, a Graphical Processing Unit, or a microprocessor), which is configured to execute an algorithm (e.g., a computer readable program code or software) to receive data, transmit data, store data, or perform methods.

In certain implementations, the computing device 1216 comprises a non-transitory computer readable medium having a series of instructions, such as computer readable program code, encoded therein. In certain implementations, the non-transitory computer readable medium comprises one or more databases. The computing device 1216 may include wired and wireless communication devices which can employ various communication protocols including near field (e.g., "Blue Tooth") or far field communication capabilities.

By way of example, the computing device 1216 includes a processor 1206, a non-transitory computer readable medium 1208, an input/output means (e.g., a keyboard, a mouse, a stylus and touch screen, or a printer) 1212, and a database 1210. The processor accesses executable code stored on the non-transitory computer readable medium 1208 of the computing device 1216, and executes one or more instructions 1214 to, for example, electronically communicate with the intra-luminal pressure sensor 1220.

In some implementations, the database 1210 can be a consolidated and/or distributed database. In some implementations, the database 1210 can be implemented as a database that is local to the computer readable medium 1208 and/or can be implemented as a database that is remote to the computer readable medium 1208. In some implementations, the database 1210 can be encoded in a memory. The database 1210 may be encoded in one or more hard disk drives, tape cartridge libraries, optical disks, or any suitable volatile or nonvolatile storage medium, storing one or more databases, or the components thereof, or as an array such as a Direct Access Storage Device (DASD), redundant array of independent disks (RAID), virtualization device, . . . etc. The database 1210 may be structured by a database model, such as a relational model or a hierarchical model.

In some implementations, one or more portions of the computer device 1216 includes a hardware-based module (e.g., a digital signal processor (DSP), a field programmable gate array (FPGA)) and/or a software-based module (e.g., a module of computer code, a set of processor-readable instructions that can be executed at a processor). In some implementations, one or more of the functions associated with, for example, the computer device 1216 is performed by different modules and/or combined into one or more modules.

In certain implementations, computer program readable code, such as instructions 1214, resides in non-transitory computer readable medium 1208, wherein those instructions are executed by the processor 1206 to perform one or more of steps recited in FIGS. 8 and/or 13. Examples of computer readable program code include, but are not limited to, micro-code or micro-instructions, machine instructions, such as produced by a compiler, code used to produce a web service, and files containing higher-level instructions that are executed by a computer using an interpreter. For example, implementations may be implemented using Java, C++, or other programming languages (e.g., object-oriented programming languages) and development tools. Additional examples of computer code include, but are not limited to, control signals, encrypted code, and compressed code.

Figure 13:
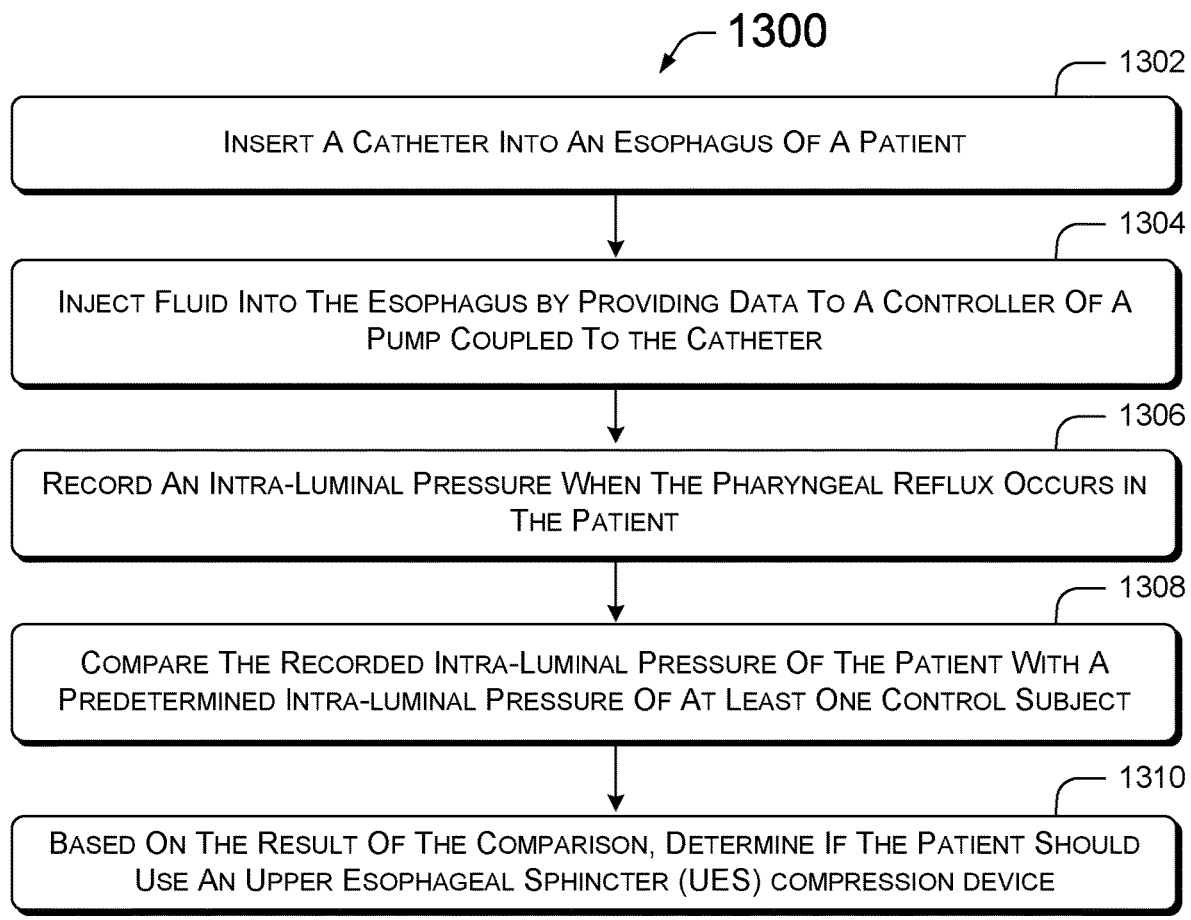
FIG. 13 is summary of a method for diagnosing UES pathology.

Referring to FIG. 13, a method 1300 summarizes steps for determining esophageal pressure. At step 1302, a catheter is inserted into an esophagus of a symptomatic patient. The catheter may be introduced into the esophagus via an orifice in the head of the patient. To illustrate, about 2% lidocaine is applied to a more patent nostril of the symptomatic patient and a manometric assembly is introduced through the nose of the symptomatic patient, positioning the intra-luminal pressure sensor within the UES such that the manometric port immediately proximal to the sleeve is positioned about 2 cm above the UES high-pressure zone. An injection port, esophageal tips, and a sleeve sensor can be connected to pressure transducers in line with a minimally compliant pneumohydraulic pump (e.g., Arndorfer Medical Specialties, Greendale, Wis.), for example.

At step 1304, fluid is injected into the esophagus. In certain implementations, data is provided to the controller of the pump to initiate an injection of fluid into the catheter 1202. For example, a dial on the pump may be turned to increase the pressure of the fluid injected into the catheter or a driver of the pump may be programmed to inject the fluid into the esophagus. In one implementation, an onset and offset of fluid injection and intra-luminal UES pressure are recorded on chart paper run at a speed of 25 mm/s, providing an equivalent of 40 milliseconds for each millimeter distance on the chart paper. Alternatively, or in combination, the onset and offset of the fluid injection and the intra-luminal UES pressure may be recorded automatically by the computing device 1216 communicatively connected to the intra-luminal pressure sensor 1220 and/or the controller 1222.

At step 1306, the intra-luminal pressure that is recorded when the pharyngeal reflux occurs in the symptomatic patient. For example, the physician my ask the symptomatic patient to signal when the pharyngeal reflux occurs. When the pharyngeal reflux occurs, the physician reads the intra-luminal pressure value and records it. Alternatively, or in combination, the intra-luminal pressure sensor intermittently communicates indicia about intra-luminal pressure to the computing device 1216 (FIG. 12). When the pharyngeal reflux occurs, the physician flags the point in time via an input means 1212 to the computing device 1216. In this manner, the pharyngeal reflux is associated with an intra-luminal pressure detected by the intra-luminal pressure sensor when the pharyngeal reflux occurs in the symptomatic patient. Other means of recording and associating of the data is also contemplated.

At step 1308, the recorded intra-luminal pressure of the symptomatic patient is compared with a predetermined intra-luminal pressure of at least one control subject. As previously stated, the predetermined intra-luminal pressure may be an algorithmic combination of one or more intra-luminal pressures measured when a pharyngeal reflux occurs in corresponding control subjects. To illustrate, the control subjects may be a plurality of healthy individuals. Here, the predetermined intra-luminal pressure is an average of the intra-luminal pressures measured when pharyngeal refluxes occur in the corresponding healthy individuals.

At step 1310, a determination is made whether the symptomatic patient should use a UES compression device based on the result of the comparison of step 1308. For example, if the intra-luminal pressure of the symptomatic patient is below that of the predetermined intra-luminal pressure of the control subjects, the physician may prescribe usage of the UES compression device. Here, steps 804-812 of FIG. 8 may be implemented to issue the prescription.

To illustrate, the symptomatic patient and the control subject can each be placed in a supine position and instructed to signal when a pharyngeal reflux is perceived. For each, a pharyngeal reflux can be simulated by infusing normal saline (e.g., between about 10 to 60 mL) and/or air (e.g., between about 10-50 mL) into the esophagus. The infusion may be at a predetermined rate, such as a rapid injection or slow injection, at a predetermined temperature (e.g., 0-60° C.). The UES and esophageal pressures can be monitored by high resolution intraluminal manometry, for example. Pharyngeal reflux/regurgitation can be monitored by high resolution esophagopharyngeal impedance recording, for example. The fluid delivery into the esophagus may be via: rapid pulse and/or slow continuous injection, for example. To illustrate, a pulse injection starts with about 0.05 mL of fluid, followed by about 0.1 mL of fluid. Subsequently, the volume is increased by about 0.1 mL increments until an irrepressible swallow occurred. Slow continuous infusion has a rate of about 5.5 mL/min until an irrepressible swallow occurs. Each injection starts at about 5 to 10 seconds after the UES pressure returns to baseline following a swallow, and the subjects withhold swallowing as long as possible. The fluid temperature may be predetermined, such as 0° C., 37° C., and 60° C.

After positioning the sleeve catheter, the control subject and/or the symptomatic patient is monitored for 10 minutes for adaptation. The corresponding changes in UES pressure (e.g., three of three injections) in response to various volumes of pharyngeal water injections is determined. The time and/or duration of the symptomatic patient's and the control subject's perceived pharyngeal reflux is recorded along with the corresponding intra-luminal pressure.

A comparison of the corresponding intra-luminal pressures of symptomatic patients and control subjects may reveal a variance. The variance may depend on whether the pharyngeal reflux occurred due to rapid versus slow fluid injections. Table 1 below shows results of a study comparing a group of symptomatic patients (8 symptomatic patients; 51±20 years old; 2 Female) with control subjects (12 control subjects; 25±5 years old; 6 Female) reported in percent instances that either UES relaxation (R) or Contraction (C) occurred. The difference between the two study groups is statistically significant ($p<0.05$). Here, the symptomatic patients, but not the control subjects, reported pharyngeal reflux during both slow and rapid esophageal fluid infusion. The UES contraction (C) was absent during slow infusion in symptomatic patients. All rapid fluid infusions produced UES contraction in the control group, while only 70-75% of rapid fluid infusions produced a UES contraction in symptomatic patients. The UES response to air distension, however, was relaxation (R) in both groups.

TABLE 1

| | Rapid Inj 10 ml (air) (%) | | Rapid Inj 20 ml (air) (%) | | Rapid Inj 30 ml (air) (%) | | Rapid Inj 10 ml (saline) (%) | | Rapid Inj 20 ml (saline) (%) | | Rapid Inj 30 ml (saline) (%) | | Slow Inj 60 ml (saline) UES Contraction (%) | Subjective Regurgitation. (%) |
|---|---|---|---|---|---|---|---|---|---|---|---|---|---|---|
| | C | R | C | R | C | R | C | R | C | R | C | R | | |
| Controls Subjects | 6 | 94 | 0 | 100 | 0 | 100 | 94 | 0 | 100 | 0 | 100 | 0 | 100 | 0 |
| Sympt. Patients | 0 | 100 | 0 | 100 | 0 | 100 | 75 | 25 | 71 | 29 | 75 | 25 | 0 | 100 |

The UES response to slow esophageal fluid distention is defective in symptomatic patients with complaints of regurgitation and supraesophageal complications, allowing escape of refluxate into the pharynx. Therefore, in this implementation, the UES response to esophageal slow fluid infusion can serve as a test for recognizing this defect, for example.

Reference throughout this specification to "one implementation," "an implementation," or similar language means that a particular feature, structure, or characteristic described in connection with the implementation is included in at least one implementation. Thus, appearances of the phrases "in one implementation," "in an implementation," "certain implementation," and similar language throughout this specification may, but do not necessarily, all refer to the same implementation.

It should be understood that the disclosed implementations can be performed in the form of control logic, in a modular or integrated manner, using software, hardware or a combination of both. The steps of a method, process, or algorithm described in connection with the implementations disclosed herein may be embodied directly in hardware, in a software module executed by a processor, or in combination of the two. The various steps or acts in a method or process may be performed in the order shown, or may be performed in another order. Additionally, one or more process or method steps may be omitted or one or more process or method steps may be added to the methods and processes. An additional step, block, or action may be added in the beginning, end, or intervening existing elements of the methods and processes. Based on the disclosure and teachings provided herein, a person of ordinary skill in the art will appreciate other ways and/or methods to implement the present invention.

The schematic flow chart diagrams included are generally set forth as a logical flow-chart diagram (e.g., FIGS. 8 and 13). As such, the depicted order and labeled steps are indicative of one implementation of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method (e.g., FIGS. 8 and 13). Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The described features, structures, or characteristics of various implementations may be combined in any suitable manner. In the following description, numerous specific details are recited to provide a thorough understanding of implementations. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the various described implementations.

It is understood that the examples and implementations described herein are for illustrative purposes only and that various modifications or changes in light thereof will be suggested to persons skilled in the art and are to be included within the spirit and purview of this application and scope of the appended claims.

I claim:

1. A method for using a compression device, the method comprising:
    positioning a cushion of a compression device over a cricoid of a patient;
    compressing the cricoid of the patient with a predetermined amount of pressure, using the cushion of the compression device;
    generating an intra-liminal pressure of the patient from the compression of the cricoid of the patient with the predetermined amount of pressure, the intra-luminal pressure having a pressure in a range of 10 mmHg to 70 mmHg, wherein the intra-luminal pressure reduces pharyngeal reflux in the patient;

allowing the patient to open an Upper Esophageal Sphincter of the patient for other physiological events, while the intra-luminal pressure is generated; and relieving an impact of an abnormal or defective Upper Esophageal Sphincter anatomy, physiology, or functionality, from the generated intra-luminal pressure.

2. The method of claim 1, further comprising:

placing a band of the compression device around a neck of the patient, wherein the cushion is disposed on the band; and placing the band in tension to compress the cricoid of the patient with the predetermined amount of pressure.

3. The method of claim 1, further comprising determining a value of an indicator on the compression device, wherein the indicator is associated with the predetermined amount of pressure.

4. A method for using a compression device, the method comprising:

positioning a cushion of a compression device over a cricoid of a patient; and using the compression device to exert a predetermined amount of pressure to the cricoid to reduce pharyngeal reflux in the patient while allowing the patient to open an Upper Esophageal Sphincter of the patient for other physiological events; and using a pressure sensor to determine the predetermined amount of pressure; and repositioning the cushion of the compression device over the cricoid of the patient to reapply the predetermined amount of pressure.

5. The method of claim 4, further comprising:

avoiding a compression of vasculature structures within a neck of the patient.

6. The method of claim 4, further comprising:

generating an intra-luminal pressure of the patient from a compression of the cricoid with the compression device exerting the predetermined amount of pressure; and wherein the intra-luminal pressure is in a range of 10 mmHg to 70 mmHg.

7. A method for using a compression device, the method comprising:

positioning a cushion of a compression device over a cricoid of a patient;

using the compression device to exert a predetermined amount of pressure to the cricoid to reduce pharyngeal reflux in the patient while allowing the patient to open an Upper Esophageal Sphincter of the patient for other physiological events; and repeating the positioning and using steps for the patient over a period of at least days.

8. The method of claim 7, further comprising:

avoiding a compression of vasculature structures within a neck of the patient.

9. The method of claim 7, further comprising:

generating an intra-luminal pressure of the patient from a compression of the cricoid with the compression device exerting the predetermined amount of pressure; and wherein the intra-luminal pressure is in a range of 10 mmHg to 70 mmHg.

10. The method of claim 7, wherein the compression device exerts the predetermined amount of pressure to the cricoid when the patient is sleeping.

11. The method of claim 7, further comprising using a pressure sensor to determine the predetermined amount of pressure.

12. The method of claim 11, further comprising transmitting indicia about intra-luminal pressure from the pressure sensor to a computing device.

13. The method of claim 12 wherein:

the computing device is one of a server, a mainframe computer, a mobile telephone, a personal digital assistant, a personal computer, or a laptop.

14. The method of claim 12 wherein:

the computing device is a mobile telephone.

* * * * *

UNITED STATES PATENT AND TRADEMARK OFFICE
CERTIFICATE OF CORRECTION

PATENT NO. : 10,660,653 B2
APPLICATION NO. : 15/349635
DATED : May 26, 2020
INVENTOR(S) : Reza Shaker It is certified that error appears in the above-identified patent and that said Letters Patent is hereby corrected as shown below:

In the Specification

Column 1, Line 15. Please insert:
--This invention was made with government support under RR031973 and TR000055 awarded by the National Institutes of Health. The government has certain rights in the invention.--

Signed and Sealed this
Eighth Day of September, 2020

Andrei Iancu
*Director of the United States Patent and Trademark Office*